United States Patent [19]

Tamminmaki et al.

[11] Patent Number: 5,569,264

[45] Date of Patent: Oct. 29, 1996

[54] SURGICAL INSTALLATION INSTRUMENT

[75] Inventors: Markku Tamminmaki, Tampere, Finland; Peter Albrecht-Olsen, Charlottenlund; Gert Kristensen, Ebeltoft, both of Denmark; Pertti Tormala, Tampere, Finland

[73] Assignee: Biocon Oy, Tampere, Finland

[21] Appl. No.: 256,787

[22] PCT Filed: Jan. 18, 1993

[86] PCT No.: PCT/FI93/00015

§ 371 Date: Oct. 14, 1994

§ 102(e) Date: Oct. 14, 1994

[87] PCT Pub. No.: WO93/14706

PCT Pub. Date: Aug. 5, 1993

[30] Foreign Application Priority Data

Jan. 24, 1992 [FI] Finland ................... 920306

[51] Int. Cl.⁶ ........................... A61B 17/56
[52] U.S. Cl. ............... 606/104; 606/86; 606/169
[58] Field of Search ............... 606/104, 72, 73, 606/75, 96, 99, 100, 86, 169, 171, 178

[56] References Cited

U.S. PATENT DOCUMENTS

| | | | |
|---|---|---|---|
| 2,248,054 | 7/1941 | Becker | 606/104 X |
| 3,892,232 | 7/1975 | Neufeld | 606/104 X |
| 4,298,074 | 11/1981 | Mattchen | 606/104 X |
| 4,873,976 | 10/1989 | Schreiber | |
| 5,059,206 | 10/1991 | Winters | |
| 5,152,765 | 10/1992 | Ross et al. | 606/99 |
| 5,180,388 | 1/1993 | DiCarlo | 623/16 |

FOREIGN PATENT DOCUMENTS 0130784  1/1985  European Pat. Off. .

*Primary Examiner*—Guy Tucker
*Attorney, Agent, or Firm*—Pollock, Vande Sande & Priddy

[57] ABSTRACT

A surgical instrument for installing an implant in a living tissue. The instrument includes a frame including an installation channel that is adapted for receiving the implant and is adapted to be placed in connection with the tissue. The implant is inserted in the tissue when it exits the installation channel. The frame includes an installation end. Apparatus produces a reciprocating movement that is transmitted to the implant to produce a periodic movement in the implant. An installation member conveys an external installation force to the implant for installing the implant. The installation member is insertable in the installation channel.

15 Claims, 3 Drawing Sheets

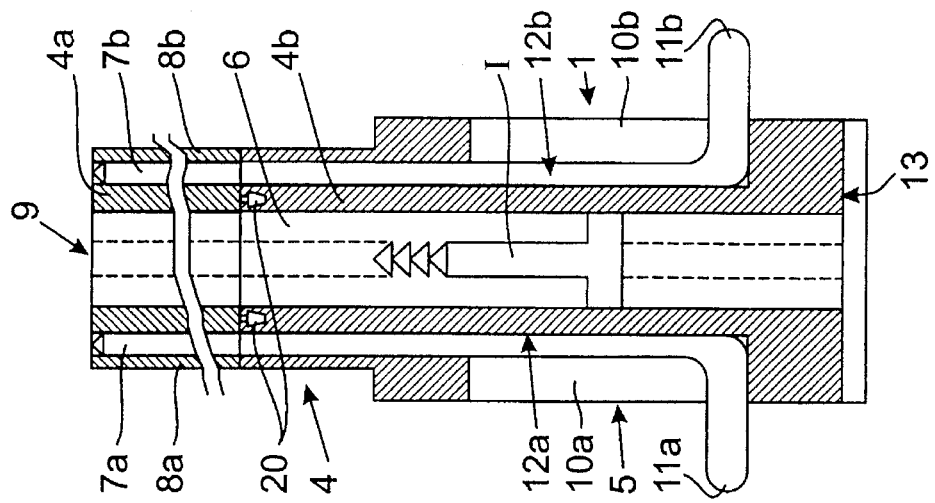

5,569,264

SURGICAL INSTALLATION INSTRUMENT

FIELD OF THE INVENTION

This application is a 35 U.S.C. 371 application of PCT/FI96/00015 filed on Jan. 18, 1993.

The present invention relates to a surgical instrument for installation of a surgical implant in a living tissue, particularly in connection with a surgical operation. The installation instrument comprises a frame with an installation channel, in which the implant is inserted in the beginning of installation. The instrument further comprises an installation part arranged to be inserted in the installation channel and to convey an external force needed for the installation of the implant to the implant. The frame is placed in connection with the tissue in a manner that the implant is inserted in the tissue when it exits the installation channel at the installation end of the frame.

In the context of the present invention, living tissue refers particularly to bone, ligament, connective tissue, synovial or joint tissue, muscular tissue, as well as others. Further, important fields of applying the invention include corrective surgery of meniscal rupture as well as bone surgery as treatment of bone fractures. The installation instrument of the invention is suitable for use in arthroscopic surgery. In this invention, implant refers to a usually elongated macroscopic piece that is suitable to be surgically installed with a force effective thereon. The force moves the implant essentially in the direction of its largest dimension into the tissue.

BACKGROUND OF THE INVENTION

Implants of this kind typically include rod-shaped and arrow-shaped implants. As to arrow-shaped implants, reference is made to U.S. Pat. No. 4,873,976. This patent discloses an arrow-shaped implant and a method for its installation. The implant and method are to be used particularly in the repairing surgery of meniscal rupture. The implant is typically manufactured of at least martially bioabsorbable polymer material.

In surgery, it is generally known to use installation instruments, typically manufactured of metal, for installing macroscopic implants, such as rods, hooks, pins, bolts and the like. Such implants are used in living tissues to connect operated or damaged tissues with each other or with other tissues. In such surgical installation instruments, the implant is typically placed at the initial stage either in part or wholly inside an installation channel in the installation instrument. The implant is forced from the installation instrument into the tissue by tapping manually with a hammer. A special, typically piston-like, installation part conveys the force generated with the hammer to the implant and, thus, forces the implant to penetrate into the tissue. It is also known to use an application whereby the implant is forced into the tissue by one powerful, quick stroke effected on the implant. The stroke maybe produce mechanically, pneumatically, hydraulically or electromagnetically, for example.

However, the surgical installation instruments of prior art used for installation macroscopic implants into a tissue nave certain disadvantages. If the surgeon uses a manual installation instrument, he/she needs both of his/her hands for controlling the instrument. With one hand, the surgeon must support the frame of the surgical implant, wherein the surgical implant is inserted, at least partly, in the beginning of the installation operation. With the other hand, the surgeon must tap the hammer or a corresponding tool, thus directing the force required for the transmission of the implant and conveyed by an installation part into the implant. Consequently, the surgeon cannot use his/her own hands to keep in position that part or parts of the tissue that he/she will attach to each other with the implant. Thus, the surgeon must usually have an assistant who keeps the parts of the tissue in position. As a result, the direct feel of the surgeon to the reactions of the tissue is essentially diminished as the operation proceeds. If the surgeon alternatively uses an installation instrument which forces the implant by one stroke into the tissue, his/her control over the installation procedure is also very poor. The lack of control results in an inability to change the direction or position of the implant as the installation operation proceeds. Additionally the installation operation cannot be stopped after the implant has been triggered.

SUMMARY OF THE INVENTION

It is an object of this invention to present a new kind of surgical installation instrument for use in the installation of macroscopic implants. The present invention overcomes disadvantages of installation instruments of prior art as well as factors delimiting the safety of patients. For achieving this aim, the installation instrument according to the invention is primarily characterized in that the installation part comprises means for connecting the installation part to a power transmission part arranged to perform a reciprocating movement. The reciprocating movement is arranged to be transmitted as a periodical movement of the implant from the installation channel through the installation end of the frame into the tissue.

Application of the surgical installation instrument in the manner described above provides several advantages over the instruments of prior art.

Using an installation instrument of the invention, the surgeon can install an implant into a tissue by one hand. This permits the surgeon to maintain his other hand in position those parts of the tissue through which the surgeon intends to force the implant. The surgeon can, thus, control the installation operation better than with present methods. Improved control over the installation permits the surgeon to correct the position of the tissues during the installation operation, when necessary. Also, the penetration of the implant effected by successive, quick strokes enables the surgeon to control the installation operation better than before, because he/she can, for example, change the direction of the installation instrument and/or the implant during the installation operation or interrupt the operation, if necessary. This may be required, for example, in a case when the tissues to be attached to each other are displaced for any reason during the operation.

The advantages of the installation instrument exerting quick reciprocating or vibrational movement can have the following theoretical basis: According to the viscoelastic theory, the modulus of viscoelastic material increases with an increase in the velocity of dynamic stress. In practice, this means that when an arrow-shaped implant is slowly penetrated into a viscoelastic connective tissue such as meniscal tissue, the meniscal tissue reacts as a soft material, yielding and tending to bend away from the implant penetrating into it. On the other hand, when the implant is vibrated step-by-step into the tissue utilizing a reciprocating movement by quick strokes of the installation instrument, the meniscal tissue will not react fast enough to the movement of the arrow-shaped implant in the manner of a soft material.

Rather, the meniscal tissue will react as a hard material, not yielding with the forward movement of the implant anywhere near the extent as in manual penetration or stroke. The implant thus penetrates the meniscal tissue, or a preliminary hole made in it, easily without causing extensive transformation of the surrounding tissue.

In a particularly advantageous embodiment, the frame of the installation instrument further comprises at lease one arresting means that is in the operational position of the frame. According to this embodiment, the installation part is inserted inside the installation channel, in contact with the tissue, in order to arrest the installation end of the frame in position in relation to the tissue during installation of the implant. As the frame can be locked in the installation end by the arresting means into the tissue for the time of the operation, the surgeon can secure the correct position of the installation channel before the actual phase of installing the implant.

Further, according to a preferred embodiment of the invention, at least one arresting means in the surgical installation instrument is arranged to be movable and lockable in relation to the frame. According to this embodiment the said arresting means in the non-operational position is placed inside the installation end of the frame. In the operational position, the arresting means from the installation end of the frame. In this application, it is possible to place the arresting means inside a tissue, particularly a soft tissue, in a way required by the surgical operation and the dimensions of the tissue in question. The arresting means can be advantageously, locked at different penetration depths in relation to the frame in its operational position. For this purpose, the frame can be equipped with several locking means cooperating with a transfer and locking means placed in the arresting means and preferably controlled manually. The locking means can be locked in position for locking the arresting means in a desired operational penetration depth.

Further, according to another preferred embodiment of the invention, the installation instrument further comprises at least one needle-like element. The needle-like element has a cross-section at least partly formed in a manner such that the needle-like element can be placed, via the installation channel or a part thereof, to bypass the installation end of the frame in order to make a preliminary hole or a like in the tissue before the installation of the implant. The installation end of the frame is placed in the installation position of the implant and arrested by at least one arresting means. This application provides the advantage of a smaller force required for the series of strokes by the installation part on the implant. As a natural consequence, the risk of an implant to be directed into an incorrect position and damaged is substantially reduced, because the forces effective upon it during installation are reasonable. This embodiment is particularly advantageous in connection with operations on tough fibrous tissues, such as meniscus, in which the margin of error is very small.

Further, according to still another advantageous embodiment, the frame of the installation instrument is at least partially formed of a transparent material.

Installation instruments of prior art are manufactured of metal material, particularly stainless steel. For this reason, these installation instruments have the disadvantage of not enabling the surgeon to evaluate visually the progress of the installation of the instrument and the condition of the implant. In particular, lack of visual contact with at least that part of the installation instrument where the implant is situated, that is the installation end of the installation frame of the instrument, complicates arthroscopic operations. Arthroscupic operations are performed inside a joint by introducing a installation instrument into the arthral chamber through a small inclision. The stages of the operation are controlled by means of a special arthroscopic instrument that is introduced into the arthral chamber either through the same or another small incision. Consequently, the surgical installation instrument of the present invention can also be used to avoid this adverse factor present in installation instruments of prior art. Thus, the present invention can further increase reliability and safety of the installation to the patient.

Some advantageous embodiments of the surgical installation instrument of the invention are further presented below.

BRIEF DESCRIPTION OF THE DRAWINGS

In the following description, the surgical installation instrument of the invention will be illustrated further with reference to the embodiments shown in the appended drawings. In the drawings, FIG. 1 shows a schematic perspective view of a first embodiment of the surgical installation instrument;

FIG. 2 illustrates the cross-section of the embodiment of the frame of the installation instrument shown in FIG. 1 in a longitudinal direction;

DETAILED DESCRIPTION OF THE INVENTION

Figure 4:
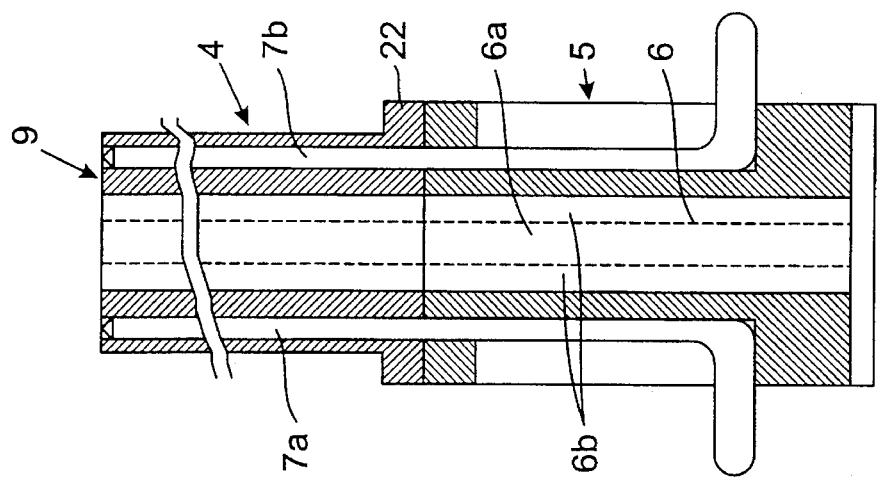
FIG. 4 illustrates the cross-section of the embodiment the frame of the installation instrument shown in FIG. 3 in a longitudinal direction.

With reference to FIG. 1, the installation instrument of the invention comprises as main parts a frame 1 and an installation part 2. FIG. 1 also illustrates two needle-like elements 3a, 3b of the surgical installation instrument.

The frame 1 comprises a combination of an elongated installation frame 4 and an operational frame 5. The frame 1 is penetrated by an installation channel 6. The cross-sectional form of the installation channel corresponds to the shape of the outer surface of the implant I as seen in the direction of the longitudinal axis of the implant. In the embodiment in FIG. 1, the installation frame 4 has a flat cross-sectional form. For example, the installation frame 4 may have a rectangular or oval form. The installation channel 6 is centrally situated in the direction of the greater dimension of the installation frame such that arresting means 7a, 7b are located on both sides thereof in the same direction. The arresting means 7a, 7b can be fixedly mounted or attached or they are placed in corresponding arresting channels 8a, 8b in the frame. The arresting channels 8a, 8b extend in the direction of the installation channel. In the non-operational position, the arresting means 7a, 7b, which are rod-like elements with a sharpened head and a circular cross-sectional form, are inside the installation end 9 or the frame 1. At the point of the arresting means, there is a longitudinal groove 10a, 10b on both sides of the operational frame 5. Protruding transfer and locking means 11a, 11b are connected with the arresting means.

In the embodiment shown above, a transverse grooving 12a, 12b has been formed in the grooves 10a, 10b. Transversely grooving 12a, 12b is perpendicular to the longitudinal direction of the grooves 10a, 10b. The transfer and locking means 11a, 11b can be placed in the transfer grooving 12a, 12b when the arresting means is moved into the operational position in the longitudinal direction of the arresting channel 8a, 8b and, thus, to protrude from the installation end 9 of the frame 1. The arresting means are 7a7b locked by moving the transfer and locking means 11a, 11b around the longitudinal axis of the arresting means into a desired groove of the transverse grooving 12a, 12b.

Figure 3:
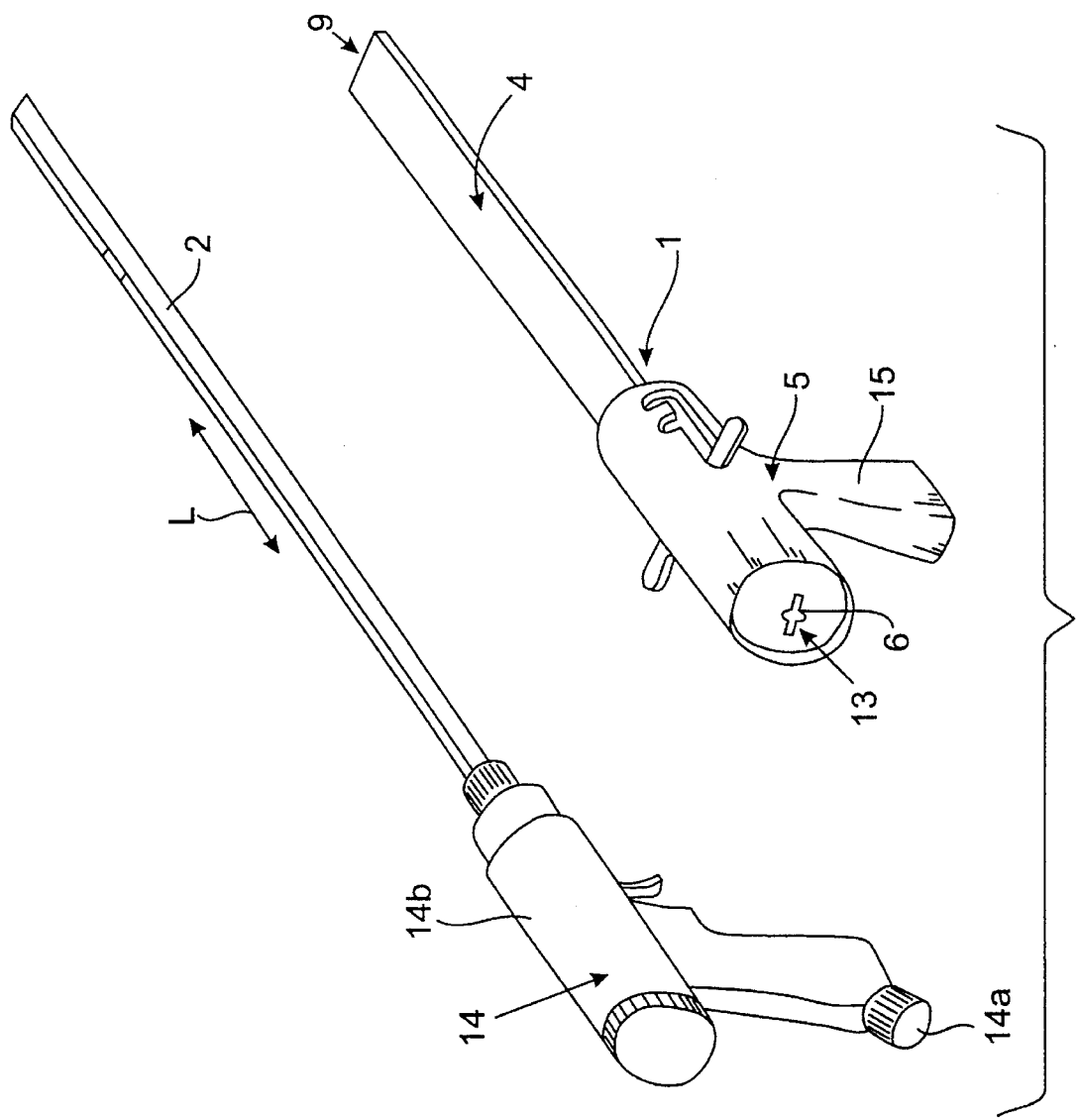
FIG. 3 shows a perspective view of a second embodiment of the surgical installation instrument, where the installation part is fixed in connection with a power transmission element.

As mentioned above, the other end of the installation channel 6 is placed at the supply end 13 of the operational frame in a manner such that the installation part 2 can, fixed with the power transmission part 14 shown in FIG. 3 be inserted in the installation channel.

The operational frame is further equipped with a handle 15.

In the application shown in FIG. 1, the operational frame 5 further comprises a cassette or box 16 that can be changed in connection with the operational frame. A suitable number of implants I can be placed within the box 16 in advance. In FIG. 1, one implant is illustrated inside the box 16 with broken lines. In the embodiment shown, the implant I is an arrow-shaped element having a head and a stem at opposite ends of a body. The head comprises a scutellate or corresponding arresting structure. The radial dimension of the stem is formed to exceed that of the body. In connection with a surgical operation on, for example, a meniscal rupture, as illustrated particularly in FIG. 5d, the head penetrates the meniscus at least particularly. In this procedure the stem remains outside the meniscus to prevent an unintentional movement of the implant in the direction of installation. On the other hand, the scutellate or corresponding structure of the head cooperates with the stem, exerting a compressing force on the meniscus, particularly the rupture. This contributes to the healing of the meniscus. In this connection, it should be pointed out that although the invention is illustrated with an example that is applicable particularly in surgical operations of the meniscus, it is clear that the surgical instrument of the present invention can be equally well applied in bone surgery, particularly in surgical operations on bone fractures, in connective tissue surgery and other surgery of the tissues of the musculosceletal system. Further, with reference to FIG. 1, the box 16 can comprise a spring-loaded plunger 17. Plunger 17 can keep the implants I in such an order in the box 16 that upon pulling a loading device 18 between the box 16 and the operational frame 5, for example, in the direction of arrow 19, the next implant I is moved from the box 16 into the installation channel 6 within the operational frame, as shown schematically in FIG. 2. From this position, the implant I can, for example, by using the installation part 2, be transferred to the installation end 9 of the installation channel.

In an advantageous manner, the surgical installation instrument of the invention is made to be at least partly transparent. In the embodiment shown in FIG. 1, the part at the installation end 9 of the installation frame 4 is made transparent. This transparent part 4a of the installation frame 4 can be advantageously manufactured as a disposable part that can be attached with snap-in fixing means to the stationary part 4b of the installation frame mounted on the operational frame 5. The snap-in fixing means are shown by the reference numeral 20 in FIG. 2. The transparent part 4a can be manufactured of a transparent polymer, copolymer or a polymeric mixture. Also ceramic materials are feasible materials to form the transparent part. The transparent part 4a naturally comprises a part corresponding to the cross-sectional form of the Installation channel as well as parts corresponding to the arresting channel, thereby making it functionally fully compatible with the frame 1.

FIG. 1 further illustrates the installation part 2 pertaining to the surgical instrument of the invention. Part 2 is an elongated rod-like formed piece with a cross-sectional form. The part 2 is perpendicular to the longitudinal direction of the installation frame. Preferably, the part 2 has a cross-section corresponding to the cross-sectional form and size of the installation channel 6 of the frame 1. The length of the installation part is selected so that, connected with a power transmission part 14, it can act on the implant in the installation channel, particularly the stem, for the entire length of the installation channel. The other end part of the installation part 2 is equipped with a means 21 for attaching the installation part to the power transmission part 14, shown in FIG. 3. The reciprocating movement of the power transmission part 14 is arranged in a way that the installation part 2 moves backward and forward in its longitudinal direction, as indicated by the arrow L in FIG. 3).

FIG. 3 illustrates an embodiment of the frame 1 where the implant is fed into the installation channel through an opening in the supply end 13 in the installation channel. Using the installation part 2 coupled with the power transmission part 14, the implant is entered into the installation end 9 of the frame 1 in the installation channel. The power transmission part 14 can be operated on a pneumatic, hydraulic and/or electromagnetic principle. The power transmission part 14 shown in FIG. 3 is arranged to work pneumatically. It has a connecting means 14a for conveying compressed air into a piston arrangement inside the frame 14b of the power transmission part 14. Power transmission parts of this kind are available in different commercial applications, for example, as reciprocating surgical bone saws. These power transmission parts can be applied minor technical modifications for use in combination with a surgical installation instrument of this invention. An example of such power transmission parts are products marketed under the trademark HALL$^R$. Power transmission parts of this kind, as well as their socket structures, in which the attaching means 21 of the installation part 2, shown in FIG. 1 is attached, are obvious to an artisan in the field and consequently not described more closely in this context.

FIG. 4 shows an alternative application for combining the installation frame 4, which is preferably transparent, and the operational frame 5. In this embodiment, the installation frame 4 is entirely formed of a transparent material, and its end is equipped with a flange 16. The installation frame 4 is attached to the end of the operational frame 5 as indicated by the broken lines in FIG. 4. The installation frame may be attached to the operation frame with a screw, for example. An advantage of this arrangement is that installation frames 4 of different shapes can be used in connection with the same operational frame 5. It is a generally known fact that curved or bent forms of the installation frame 4 may be required in certain surgical operations in order to get at the tissue to be operated on. Consequently, a solution of this kind can broaden the field of use of the surgical installation instrument. Naturally in these cases flexibility is required of the material of the arresting means so that they can adjust to the shape of the installation frame 4.

FIGS. 5a–5d illustrate schematically the phases of a surgical operation performed using a frame shown in FIGS.

Figure 5A:
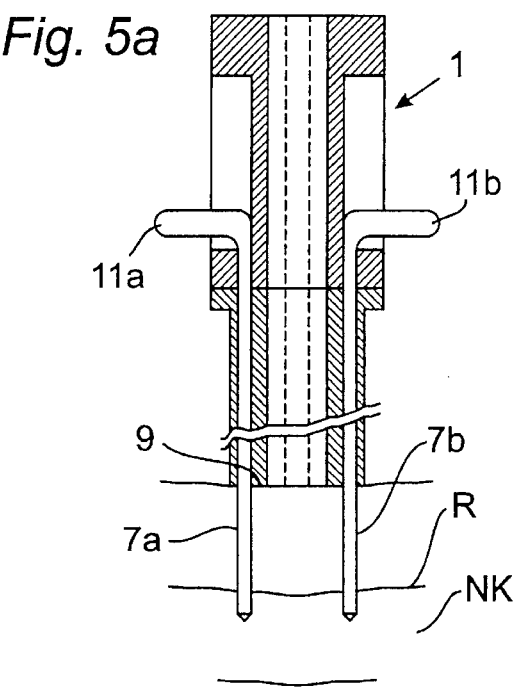
FIGS. 5a–d schematically illustrate the phases of installation of an implant, particularly an arrow-shaped implant, into the meniscus.
Figure 5B:
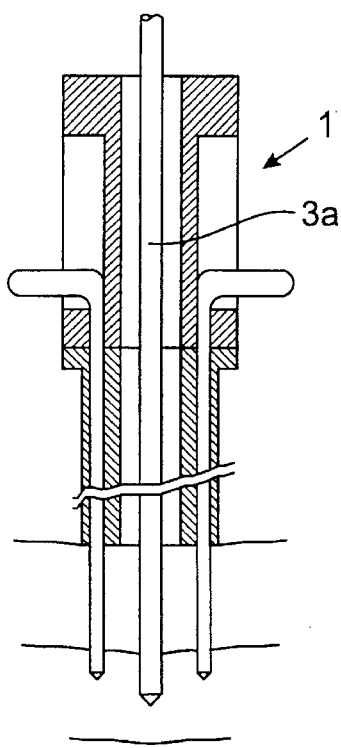
Figure 5C:
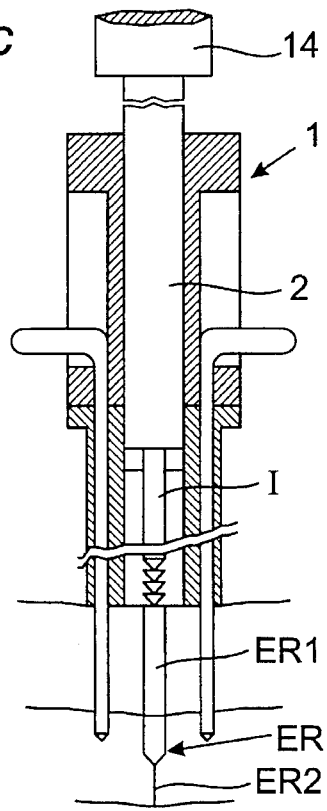
Figure 5D:
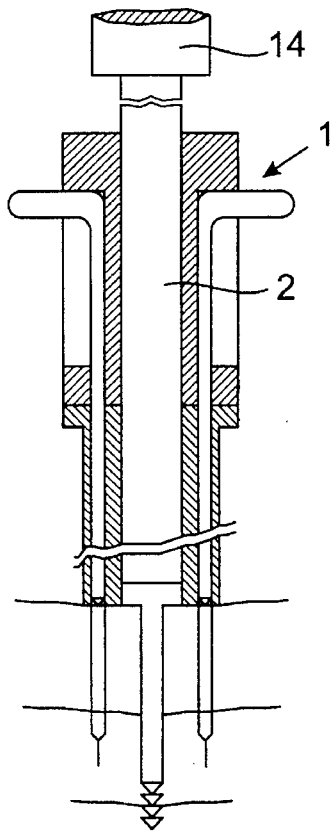

3 and 4. The operation shown in FIG. 5a–5b is a surgical repairing operation of a rupture R of the meniscus NK. This is performed preferably by arthroscopy. In the first phase shown in FIG. 5a, the arresting means 7a, 7b are pushed into the operational position by rising the transfer and locking means 11a, 11b, whereby the arresting means can extend over the rupture. In this manner, the installation end 9 of the frame 1 is locked position and at the same time the rupture R is immobilized and, thus controlled. In the next phase according to FIG. 5b, a needle-like element 3a is introduced via the installation channel 6 into the meniscus in order to make a preliminary hole. FIG. 5b illustrates the use of a needle-like element 3a. However in the embodiment shown in FIG. 5c, a needle-like element (not shown) of FIG. 1 can also be used. The needle-like element 3b comprises two needle-like elements, one inside the other. The outer element 3b' has a larger diameter. Inside the outer element it is a relatively thin needle-like element 3b". The preliminary hole is lengthened by the element 3b" after the outer needle-like element 3b' has substantially reached the center of the meniscus and passed the rupture, all the way through the meniscus. Thus, a preliminary hole ER is formed as shown in FIG. 5c. The preliminary hole ER comprises a part ER1 with a wider diameter and a part ER2 with a smaller diameter. The diameter of the needle-like element can correspond to the diameter of the body of the implant I, whereby the needle-like element can be moved in the installation channel along the wider middle section of the installation channel. This wider middle section is shown by the reference numeral 6a in FIG. 4. Particularly for the wider wing structure of the stem of the implant I, the installation channel 6 is provided with widenings shown by the reference numeral 6b in FIG. 4. Further, FIG. 5c illustrates the placement of the implant in the installation channel 6 all the way to the installation end 9 of the installation frame 4 using the installation part 2, which is coupled with the power transmission part 14. The implant I is pressed via the preliminary hole ER through the meniscus into a position shown in FIG. 5d. In this phase, the advantages of the surgical installation instrument of the present invention are obvious. The arresting means 7a, 7b ensure that the frame 1 is kept in position. The preliminary hole ER facilitates the installation of the implant. The transparent installation frame 4 provides immediate visual control of the position of the implant in the installation frame also during arthroscopy. Further, the most important operational advantage in this phase is the fact that the surgeon, while maintaining the stem of the implant I in contact with the head of the installation part 2, can observe the implant as it proceeds into the preliminary hole and stop the installation of the implant if necessary. Thus, the implant can be installed into the tissue in stages by utilizing the reciprocating movement of the installation part and the simultaneous movement in the installation channel feeding the installation part.

It is obvious that the advantages presented above apply also to many surgical operations than other meniscal operations.

The installation instrument of the invention can be modified even to a high degree. One particular alternative for a frame, especially a transparent installation frame, is to fix the arresting means in connection with the transparent frame in a manner that they protrude from the installation end 9. Thus the arresting means 11a and 11b, which can be moved and locked in relation to the frame 1, can be eliminated from the frame 1. It is also obvious that there can be one, or more than two of the arresting means 7a, 7b placed in the same frame 1 to be moved and locked in relation to the frame 1 or to the transparent installation frame protruding from the installation end 9 of the installation frame.

Obviously, the dimensions and shape of the surgical installation instrument can even vary considerably; only a few applicable alternatives are shown in the appended drawings. In the embodiment shown in the drawings, the following dimensions can be brought up within the basic dimensions. The total length of the installation frame 4 can vary between 20 and 200 mm. The width and thickness of the flat cross-section of the installation frame 4 can be typically 3 to 6 mm and and 1 to 3 mm, respectively. The length of the operational frame 5 can be 20 to 120 mm, whereby the total length of the frame 1 varies between 40 and 320 mm. The penetration depth of the arresting means can be chosen by the transverse grooving to be 5–10 mm, for example. The arrow-shaped implant used, for example, in meniscal surgery has a length of about 14 mm. The diameter of the body is about 1.5 mm. The maximum radial dimension of the stem is 3 mm. The dimension of the stem length of the wing in the axial direction being is about 1.5 mm.

One very important detail, is that according to practical measurements, good penetration of the implant into the meniscal tissue is achieved when the maximum rate of a single stroke of the vibrating movement is at least 300 meter per minute (m/min) and the frequency of the strokes is higher than 1000/min or about 17/s and, preferably about 10000–20000/min or about 170–340/s. If the stroke rate is in the order of 50 to 150 m/min, which is a typical stroke rate when slow vibration is performed manually by hitting a cylindrical piston with a suitable hammer, the piston conveying the stroke to the implant, the rate of the stroke is thus so low that the meniscal tissue reacts in a manner of a soft material, yielding and bending, whereby the implant does not properly penetrate into the tissue.

Co-pending application "Surgical implant" of the same applicant, to which reference is hereby made describes in detail the implant described above.

We claim:

1. A surgical instrument for installation of a surgical implant in a living tissue said surgical instrument comprising:

a frame including an installation channel that is adapted for receiving the implant and to be placed in connection with the tissue, whereby the implant is inserted in the tissue when it exits said installation channel;

said frame including an installation end that contacts said tissue during installation of the implant;

at least one arresting means provided in said frame for arresting said frame in relation to said tissue during installation of said implant;

means for producing a reciprocating movement that is transmitted to the implant during installation of the implant to produce a periodic movement in the implant;

an installation member insertable into said installation channel for conveying external installation force to the implant for installing the implant; and wherein said at least one arresting means is movable and lockable in relation to the frame such that in a non-operational position said at least one arresting means is located within the installation end of the frame and protrudes from the installation end of the frame in an operational position.

2. A surgical instrument according to claim 1, further comprising:

a power transmission member for transmitting said reciprocating movement to said installation member;

means for connecting said installation member with said means for producing said reciprocating movement; and means for connecting said installation member to said power transmission member.

3. A surgical instrument according to claim 1, wherein:

said installation channel penetrates said frame in a longitudinal direction;

said frame includes an arresting channel extending in a longitudinal direction to the installation end of the frame;

said at least one arresting means is a rod-like element arranged in said arresting channel, and which moves in a longitudinal direction of the arresting channel between said non-operational and operational positions.

4. A surgical instrument according to claim 1, wherein said frame includes an elongated installation frame and an operational frame.

5. A surgical instrument according to claim 1, wherein the reciprocating movement is effected by a pressurized medium selected from the group consisting of a gas and a liquid.

6. A surgical instrument according to claim 1, wherein the reciprocating movement is effected electromagnetically.

7. A surgical instrument according to claim 1, wherein said reciprocating movement is at least 300 meters/min and a frequency of said reciprocating movement is greater than 1000/min.

8. A surgical instrument according to claim 1, wherein a frequency of said reciprocating movement is about 10,000–20,000/min.

9. A surgical instrument for installing an implant in a living tissue, said surgical instrument comprising:

a frame including an installation channel that is adapted for receiving the implant and to be placed in connection with the tissue, whereby the implant is inserted in the tissue when it exits said installation channel, said frame including an installation end;

means for producing a reciprocating movement that is transmitted to the implant during installation of the implant to produce a periodic movement in the implant;

an installation member insertable into said installation channel for conveying external installation force to the implant for installing the implant;

at least one arresting means for arresting said frame in relation to said tissue during installation of said implant; and wherein said frame includes an elongated installation frame and an operational frame, said operational frame including means for moving said at least one arresting means in relation to the frame and locking means for locking said arresting means in relation to the frame.

10. A surgical instrument according to claim 9, wherein said installation frame has a flat cross-section, said installation channel is centrally arranged in a longitudinal direction of said frame relative to a greater dimension of said flat cross-sectional form;

said surgical instrument further comprising two arresting channels arranged in a longitudinal direction of said frame on opposite sides of said installation channel and wherein said arresting means is arranged in each of said installation channels and movable in a longitudinal direction, both of said arresting means including means for moving and locking said arresting means in relation to the frame.

11. A surgical instrument according to claim 9, wherein:

said operational frame further includes at least one grove;

said at least one arresting means includes a manually controllable transfer and locking means interconnected with said operational frame and transferable along said groove to achieve contact between said transfer and locking means and said locking means to lock the frame and the arresting means.

12. A surgical instrument according to claim 9, in combination with:

at least one needle-like element having a cross-section enabling it to be placed via at least a part of said installation channel to bypass the installation end of the frame to make a preliminary hole in the tissue before installation of the implant, wherein said installation end of said frame is placed in an installation position and arrested by said at least one arresting means.

13. A surgical instrument according to claim 12, further comprising a plurality of said needle-like elements arranged in connection with said surgical instrument, said needle-like elements having varying cross-sectional diameters so as to form preliminary holes of varying size and extending to different depths in the tissue.

14. A surgical instrument according to claim 9, wherein at least a portion of at least one of said frame and said installation frame is at least partially formed of a transparent material.

15. A surgical instrument according to claim 14, wherein said transparent portion of said frame or said installation frame is disposable, and at least one of said frame and said transparent portion include attaching means for attaching said frame and said transparent portion together.

* * * * *